United States Patent
Saito

Patent Number: 5,096,834
Date of Patent: Mar. 17, 1992

[54] METHOD FOR DETERMINATION OF CONCENTRATION OF SMOKE AND APPARATUS THEREFOR

[75] Inventor: Keizo Saito, Tsuchiura, Japan

[73] Assignees: Agency of Industrial Science & Technology; Ministry of International Trade & Industry, Tokyo, Japan

[21] Appl. No.: 607,855

[22] Filed: Oct. 31, 1990

[30] Foreign Application Priority Data

Sep. 30, 1988 [JP] Japan .................. 63-248439

[51] Int. Cl.[5] ............................................ G01N 21/17
[52] U.S. Cl. .................................. 436/139; 436/158; 436/159; 436/164; 436/177; 436/181; 422/93; 422/94; 356/438
[58] Field of Search ............... 436/159, 139, 143, 145, 436/164, 177, 181, 158; 422/93, 94; 356/433–435, 438

[56] References Cited

U.S. PATENT DOCUMENTS

| | | | |
|---|---|---|---|
| 3,762,878 | 10/1973 | Villalobos | 436/143 |
| 3,811,839 | 5/1974 | Di Pietro et al. | 422/59 |
| 3,963,939 | 6/1976 | Zweng et al. | 250/576 |
| 4,019,863 | 4/1977 | Jenkins et al. | 422/93 X |
| 4,040,783 | 8/1977 | Collin | 436/139 |
| 4,190,629 | 2/1980 | Strachan | 422/169 |
| 4,519,983 | 5/1985 | Espitalie et al. | 422/93 X |
| 4,617,289 | 10/1986 | Saito et al. | 502/325 |
| 4,633,706 | 1/1987 | Ito et al. | 73/28 |
| 4,747,297 | 5/1988 | Okayama et al. | 73/28 |
| 4,818,705 | 4/1989 | Schneider et al. | 436/164 |
| 4,827,760 | 5/1989 | Saito | 73/28 |
| 4,879,245 | 11/1989 | Ruse | 422/93 X |

Primary Examiner—David L. Lacey
Assistant Examiner—Jeffrey R. Snay
Attorney, Agent, or Firm—Oblon, Spivak, McClelland, Maier & Neustadt

[57] ABSTRACT

A method for the determination of smoke concentration is disclosed which comprises heating a sample smoke containing a SOF (soluble organic fraction) component and a dry soot component to a temperature not lower than the boiling point of the SOF component and not higher than the flash point of the dry soot component during the presence of the action of an oxidation catalyst thereby allowing the dry soot component in the waste smoke to be determined by measurement with a smoke tester in a state not affected by the SOF component.

3 Claims, 2 Drawing Sheets

METHOD FOR DETERMINATION OF CONCENTRATION OF SMOKE AND APPARATUS THEREFOR

This application is a continuation of application Ser. No. 07/413,486, filed on Sept. 27, 1989, now abandoned.

BACKGROUND OF THE INVENTION

1. Field of the Invention

This invention relates to a method for determining the quality of a smoke by virtue of light transmission and usable for determining the concentration, components, etc. of various exhaust smokes from diesel engines or gas turbines, for example, for regulating the concentration of the smoke, and for conducting a study on the lowering of the smoke concentration, for example, and to an apparatus for working the method.

2. Prior Art Statement

In recent years, the contamination of the environment has posed a serious social issue. The various exhaust smokes from diesel engines, gas turbines, Stirling engines, etc. are such that the concentrations and content ratios of their particulate substances vary when the conditions of the release of the exhaust smokes are varied.

As one means of determining the concentration of a smoke, the conventional light-transmission type smoke meter may be cited.

This conventional light-transmission type smoke tester is provided with a light source and a light receiving device opposed to each other as a pair across the path of a sample smoke and adapted to effect determination of a smoke concentration in the path of sample smoke by causing the path of light from the light source to the light receiving device to intersect the path of sample smoke and measuring the attenuation of the light in transmission due to the intervention of the sample smoke in the path of light.

This smoke tester has the merit of enabling continuous determination of smoke concentration on a realtime basis.

The particulate substances in the exhaust smoke include a solid dry soot component and a liquid SOF (soluble organic fraction) component. The dry soot component consists mainly of carbon and assumes a black color and the sof component consists of unburned fuel and lubricant and assumes a whitish translucent state.

The attenuation of the light in transmission, therefore, is affected in a large measure by the ratio of the concentration of the dry soot component and the concentration of the SOF component. Even where the exhaust smoke has a small dry soot component and the attenuation of the light in transmission is accordingly small proportionately, the exhaust smoke may possibly have a large SOF component. For the concentration of the particulate substance in the exhaust smoke to be accurately determined, therefore, it is necessary that the contents of the dry soot component and the SOF component in the exhaust smoke should be measured independently of each other.

This invention, intended to remedy the shortcomings of the prior art described above, aims to provide a method for the determination of the concentration of an exhaust smoke, which method is capable of allowing a smoke meter to effect continuous and accurate real-time detection of the concentration of the dry soot component and the SOF component contained in the exhaust smoke and an apparatus for working this method.

SUMMARY OF THE INVENTION

To accomplish the aforesaid object of the present invention, there is provided a method which comprises heating a sample smoke to a temperature not lower than $T_1$ and not higher than $T_2$ and, at the same time, causing an oxidation catalyst to act upon the sample smoke under the heat treatment (wherein $T_1$ stands for the boiling point of the SOF component in the sample smoke and $T_2$ for the flash point of the dry soot component in the sample smoke during the presence of the action of the oxidation catalyst) thereby deriving from the sample smoke a SOF component treated smoke in which the SOF component particles have been vaporized or burned, determining the concentration of the dry soot component in the sample smoke by subjecting the SOF component treated smoke to measurement with a smoke meter and separately subjecting the sample smoke still containing the SOF component in the untreated state to measurement with the smoke tester thereby determining the concentrations of the soot and SOF components, and finding the concentration of the SOF component in the sample smoke by comparing the concentrations of the components with the aforementioned concentration of the dry soot component.

In the present invention, the treated smoke retaining the dry soot component in the unburned state is obtained by heating the sample smoke at a temperature between the temperature $T_1$ and the temperature $T_2$ thereby gradually vaporizing the SOF component in the same smoke and burning the SOF component remaining after the vaporization with the aid of the oxidation catalyst and consequently effecting selective elimination of the SOF component from the sample smoke.

When the SOF component treated smoke is subjected to measurement with the smoke tester, since the vaporized or burned SOF component has virtually no effect on the attenuation of the light in transmission, what is obtained by this measurement is the concentration of the dry soot component in the SOF component treated smoke and, at the same time, the concentration of the dry soot component in the original sample smoke. Thus, this measurement permits the concentration of the dry soot component in the sample smoke to be accurately determined.

By dividing a given sample smoke into two portions, using one portion of the sample smoke for the determination of the concentration of the dry soot component in accordance with the method described above, and using the other portion of the sample smoke for the determination of the concentration of smoke on the basis of the attenuation of the light in transmission due to the intervention of the dry soot component and the SOF component, therefore, the concentration of the SOF component is found from the difference between the results of the two measurements and the content of the SOF component of the sample smoke is calculated from the concentration of the SOF component.

As described above, in accordance with the present invention, the contents of the dry soot component and the SOF component in the sample smoke can be accurately and continuously detected on a real-time basis by virtue of the attenuation of the light in transmission through the sample smoke.

The above and other objects and features of the invention will become more apparent from the following detailed description with reference to the accompanying drawings.

DETAILED DESCRIPTION OF THE PREFERRED EMBODIMENT

Figure 1:
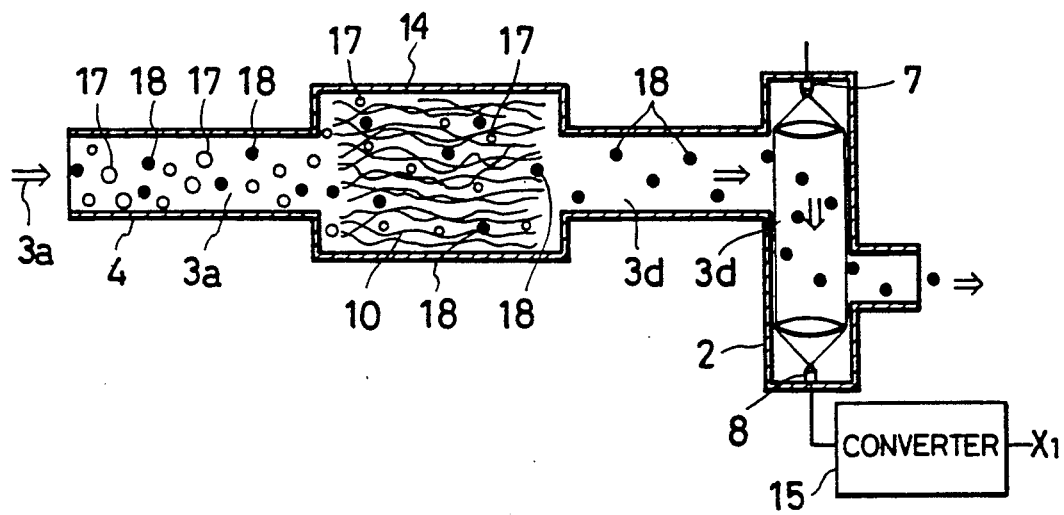
FIG. 1 is an explanatory view illustrating the method of this invention for determination of smoke concentration.

FIG. 1 illustrates the basic principle of the method for the determination of smoke concentration according to the present invention. A sample smoke 3a containing SOF component particles 17 and dry soot component particles 18 is led through a feed path (exhaust pipe) 4 to a vaporization and combustion chamber 14. Though the drawing is a model depicting SOF component particles 17 and dry soot component particles 18 as individually separated so as to facilitate the comprehension of the principle, the SOF component particles which are formed of an organic soluble substance actually are partly suspended in the form of minute particles and partly intermixed with dry soot component particles to form minute mixed particles and the SOF component particles are deposited fast on the dry soot component particles.

The vaporization and combustion chamber 14 is packed with an oxidation catalyst 10 and the interior of this chamber 14 is kept at a temperature not lower than the boiling point $T_1$ of the SOF component (200° to 250° C.) and not higher than the flash point $T_2$ of the dry soot component during the presence of the action of the oxidation catalyst (350° to 450° C.). When the sample smoke is introduced in the chamber 14, the SOF component particles 17 in the sample smoke are either vaporized or burned to convert the sample smoke into a SOF componentfree treated smoke 3d. This SOF component-free treated smoke 3d is discharged from the vaporization and combustion chamber 14 and forwarded into a smoke concentration meter 2 which is provided with a light source 7 and a light receiving device 8. In the smoke concentration tester 2, the concentration of the SOF component-free treated smoke 3d is measured. Since the SOF component which has been vaporized or burned in the vaporization and combustion chamber 14 is now in a gasified form and, therefore, has virtually no effect upon the attenuation of the light in transmission in the smoke concentration tester 2, the concentration of the dry soot component $X_1$ in the treated smoke 3d can be determined by an amplifier and A/D converter 15 on the basis of the concentration of the treated smoke 3d so measured by the smoke concentration tester 2.

Figure 2:
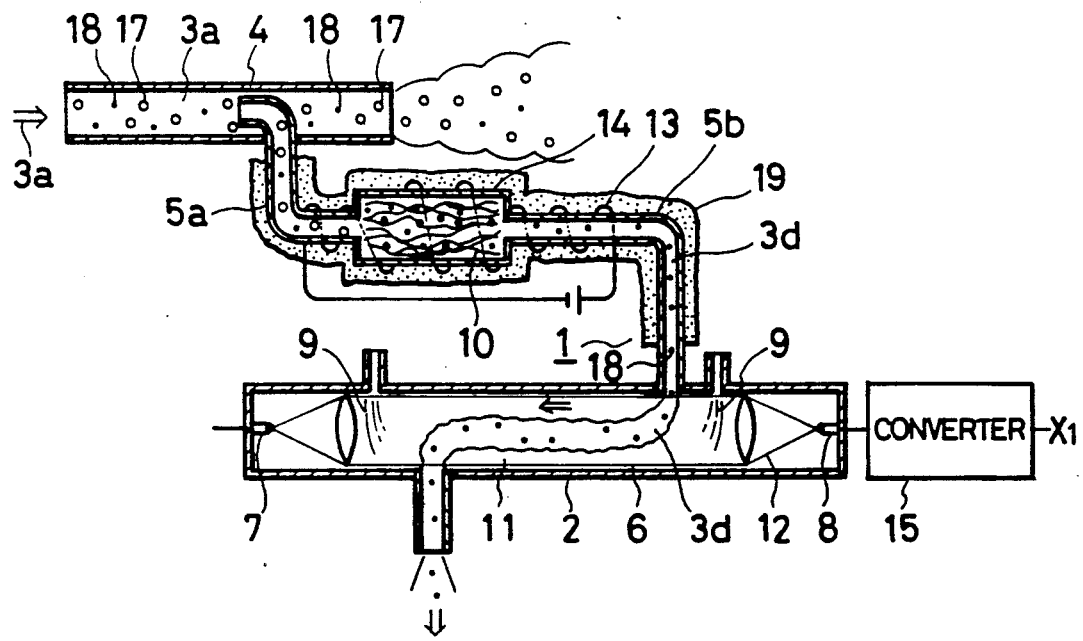
FIG. 2 is a schematic structural view illustrating an apparatus for the determination of smoke concentration as one embodiment of this invention.

FIG. 2 illustrates a typical apparatus for the determination of smoke concentration as one embodiment of this invention. An apparatus 1 is adapted to determine the concentration of the dry soot component $X_1$ of the smoke. It comprises a vaporization and combustion chamber 14 packed with an oxidation catalyst 10, a smoke concentration tester 2, a flow path 5a for introducing a sample smoke 3a, part of a smoke 3 inside the exhaust pipe 4, into the vaporization and combustion chamber 14, and a flow path 5b for introducing a SOF-free gas 3d resulting from the treatment in the vaporization and combustion chamber 14 to the smoke concentration tester 2.

The transmission light attenuation type smoke concentration tester 2 is provided with a light source 7 and a light receiving device 8 opposed to each other as a pair across a path 6 for the sample smoke (specifically the SOF-free gas) 3d so as to allow a light path 11 extending from the light source 7 to the light receiving device 8 to intersect the path 6 and attain the determination of the concentration of the smoke in the path 11 on the basis of the degree with which the transmission light 12 is attenuated by the intervention of the smoke in the light path 11. Any commercially available smoke tester adapted to fulfill the function just described can be employed as the tester 2. The path 6 is provided severally at the opposite ends thereof with an air curtain for the purpose of keeping the light source 7 and the light receiving device 8 clean at all times.

Between flow paths 5a, 5b is provided a vaporization and combustion chamber 14, which has an oxidation catalyst 10 disposed therein. A platinum metal may be used as the oxidation catalyst 10. The platinum catalyst is capable of inducing thorough combustion of the SOF component particles at temperatures in the neighborhood of 200° C.

A heater 13 is disposed on the outer periphery of the vaporization and combustion chamber 14 and the walls of the portions of the flow paths 5a, 5b preceding and following the vaporization and combustion chamber 14. This heater 13 is capable of keeping the inner temperatures of the vaporization and combustion chamber 14 and the flow paths 5a, 5b at levels not lower than the boiling point $T_1$ of the SOF component (approximately in the range of 200° to 250° C.) and not higher than the flash point $T_2$ of the dry soot component during the presence of the action of the oxidation catalyst 10 (approximately in the range of 350° to 450° C.).

The heater 13 is coated with an insulating material 19 so as to prevent the flow paths 5a, 5b and the vaporization and combustion chamber 14 from being cooled.

The apparatus 1 for the determination of smoke concentration described above is so configured that the vaporization and combustion of the SOF component particles will simultaneously proceed in one and the same vaporization and combustion chamber 14. Though this combination chamber 14 provides simplicity of construction, it is permissible to have a vaporization chamber and a combustion chamber formed separately of each other as occasion demands. Where the two chambers are formed separately of each other, it is desirable to have the vaporization chamber disposed on the upstream side in the flow path relative to the combustion chamber, heat the interior of the vaporization chamber to a temperature not lower than $T_1$ and not higher than $T_2$ so as to have as large a portion of the SOF component particles 17 as possible treated by vaporization, and enable the part of the SOF component particles remaining after the vaporization to be treated by combustion in the combustion chamber disposed on the downstream side in the flow path and provided with the oxidation catalyst. In this manner, the sample smoke can be easily treated thoroughly even when the sample smoke has a low oxygen content. Further, since the flash point of the SOF component during the presence of the action of the oxidation catalyst is about 200° C., the combustion chamber is not required to be provided on the outer periphery thereof with a separate heater. By simply keeping the portion of the flow path issuing from the vaporization chamber warm with an insulating material, the sample smoke is enabled to come into contact with the oxidation catalyst inside the combustion chamber at a temperature exceeding 200° C., with the result that the SOF component particles will be burned and gasified sufficiently.

When the oxidation catalyst is used for the removal of the SOF component particles as described above, the SOF component can be treated selectively without inducing any substantial loss of the dry soot component or producing any effect upon the attenuation of the light in transmission. Thus, the concentrations of the dry soot component and the SOF component can be determined accurately.

The method for the determination of smoke concentration by the use of the apparatus 1 described above is executed as follows.

The sample smoke 3a introduced in the flow path 5a heated with the heater 13 to elevate the temperature of the sample smoke 3a to a level not lower than the boiling point $T_1$ of the SOF component thereof and not higher than the flash point $T_2$ of the dry soot component during the presence of the action of the oxidation catalyst 10 and, at the same time, the oxidation catalyst 10 is caused to act upon the sample smoke and thereby vaporize or burn the SOF component particles 17. Consequently, the sample smoke 3a is converted into a SOF component treated smoke 3d in which the dry soot component 18 in the sample smoke 3a remains in the unburned state. By subjecting this SOF component treated smoke 3d to measurement with the transmission light attenuation type smoke tester 2, the concentration of the dry soot component in the sample smoke 3a can be detected without being affected at all by the SOF component.

Now, the method for attaining real-time independent detection of the concentrations of the dry soot component and the SOF component contained in the sample smoke by the use of the method described above will be explained herein below with reference to FIG. 3.

Figure 3:
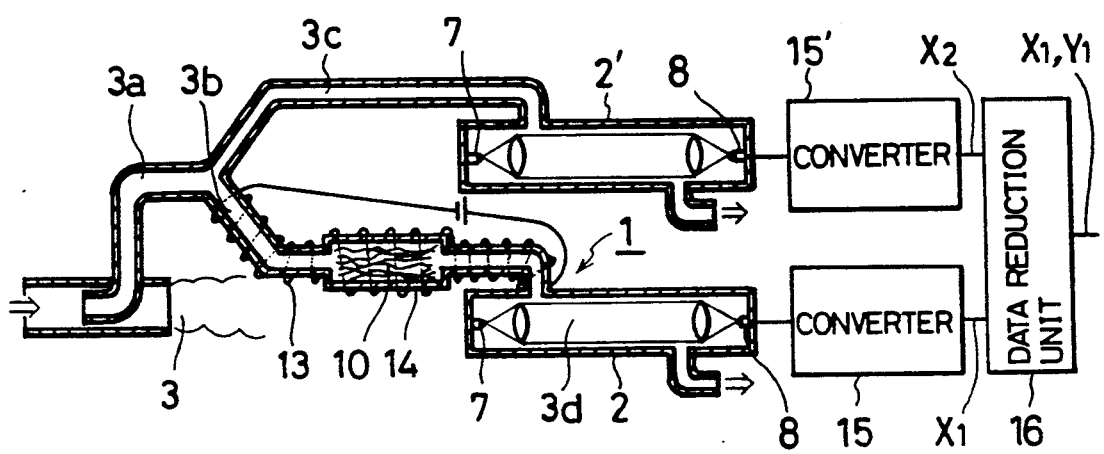
FIG. 3 is a schematic structural view illustrating another apparatus for the determination of smoke concentration as another embodiment of this invention.

As illustrated in FIG. 3, the sample smoke 3a is divided into sample smokes 3b and 3c. One sample smoke 3b is forwarded to the smoke concentration measuring apparatus 1 which comprises the combustion and vaporization chamber 10 and the smoke tester 2, to effect selective combustion of the SOF component and measurement of the concentration $X_1$ of the dry soot component. The other sample smoke 3c is directly subjected to measurement with a transmission light attenuation type smoke meter 2' to effect determination of the total smoke concentration (dry soot+SOF), $X_2$, in accordance with the attenuation of the light in transmission due to the intervention of the dry soot component and the SOF component. The difference between the total smoke concentration $X_2$ obtained at an amplifier and A/D converter 15' and the concentration $X_1$ obtained at an amplifier and A/D converter 15 of the dry soot component, namely $X_2-X_1$, represents the concentration of the SOF component in the sample smoke 3c.

When the concentration of the dry soot component and the concentration of the SOF component which bring about one same attenuation of the light in transmission in the measurement with the transmission light attenuation type smoke tester 2, 2' are subjected to conversion in the data reduction unit 16, therefore, the concentration $Y_1$ (content) of the SOF component can be easily obtained.

Figure 4:
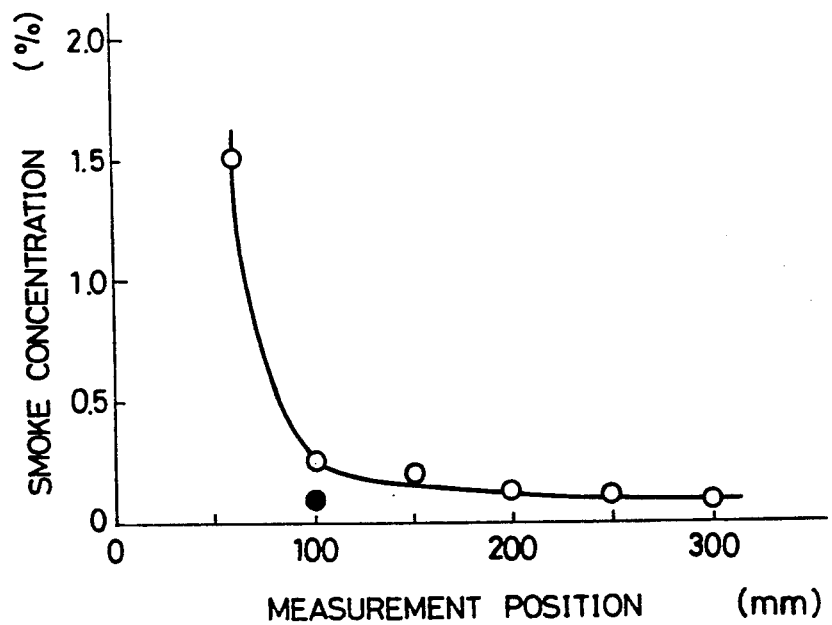
FIG. 4 is a graph showing the effect manifested by liquid drops incorporated in the exhaust smoke upon the smoke meter.

FIG. 4 is a graph showing the results of an experiment conducted by preparing a model exhaust gas having a SOF component overlapped on soot (soot component) by the incorporation of minute liquid particles in an exhaust smoke (about 200° C.) from a diesel engine and testing this model exhaust smoke for the effect of the minute liquid particles (steam) on the result of measurement with a smoke meter. From this graph, it is clearly noted that the smoke concentration which was about 1.5% at a position about 60 mm from the outlet of the exhaust pipe decreased to about 0.25% at a position about 100 mm from the same outlet, indicating that the minute liquid particles were substantially wholly vaporized and ceased to have any effect on the ratio of imperviousness. The solid circle (●) in the graph represents the concentration of the exhaust smoke determined for comparison in the absence of the incorporation of minute liquid particles.

The data of this graph imply that the amount of the SOF component released in the exhaust smoke can be determined by inversing the procedure of this invention, namely by measuring the ratio of imperviousness obtained when the SOF component is vaporized and burned in the vaporization and combustion chamber and the ratio of imperviousness obtained when the SOF component is not vaporized or burned and then finding the difference between the two ratios of imperviousness.

As clearly seen from the description given above, this invention accomplishes the determination of the concentration (content) of the SOF component by first finding the concentration of the dry soot component in the sample smoke and subsequently calculating the concentration of the SOF component on the basis of the concentration of the dry soot component. Thus, the concentrations of the dry soot component and the SOF component can be accurately and continuously detected without being affected by the degree of the attenuation of the light in transmission.

What is claimed is:

1. A method for the determination of concentrations of a SOF component and a dry soot component contained in smoke, comprising the steps of:

dividing said smoke into a first portion and a second portion;

heating said first portion of said smoke in the presence of an oxidation catalyst to a temperature not lower than the boiling point of a SOF component contained in said first portion and not higher than the flash point of a dry soot component contained in said first portion when said oxidation catalyst acts on said dry soot component, thereby combusting and evaporating said SOF component into a SOF component not causing light attenuation and keeping said dry soot component substantially intact;

transmitting light through the resultant first portion to detect a light attenuation ratio of said first portion, thereby finding the concentration of said dry soot component;

transmitting light through said second portion of said smoke to detect a light attenuation ratio of said second portion, thereby finding the concentration of SOF and dry soot components contained in said second portion; and determining the concentration of said SOF component contained in said smoke from the difference between the two found concentrations.

2. The method according to claim 1, wherein said temperature is in the range of 250° to 350° C.

3. An apparatus for the determination of concentrations of a SOF component and a dry soot component contained in smoke, comprising:

means for dividing said smoke into a first portion and a second portion;

an oxidation catalyst heating means for heating said first portion of said smoke to a temperature not lower than the boiling point of a SOF component contained in said first portion and not higher than the flash point of a dry soot component contained in said first portion;

a first transmission light attenuation smoke tester for determining the concentration of said dry soot component in said first portion of said smoke;

a second transmission light attenuation smoke tester for determining the concentration of SOF and dry soot components contained in said second portion of said smoke; and means for determining the concentration of said SOF component contained in said smoke from the difference between the two concentrations determined by said first and second transmission light attenuation type smoke testers.

* * * * *

UNITED STATES PATENT AND TRADEMARK OFFICE
CERTIFICATE OF CORRECTION

PATENT NO. : 5,096,834
DATED : March 17, 1992
INVENTOR(S) : Keizo Saito

It is certified that error appears in the above-identified patent and that said Letters Patent is hereby corrected as shown below:

On the Title page, item [63]
The Related U.S. Application Data has been omitted, should be, --Continuation of Ser. No. 413,486, September 27, 1989, abandoned.--

Signed and Sealed this

Twenty-eighth Day of September, 1993

Attest:

BRUCE LEHMAN

Attesting Officer     Commissioner of Patents and Trademarks